United States Patent [19]

Saito et al.

[11] Patent Number: 5,780,301
[45] Date of Patent: Jul. 14, 1998

[54] SERUM-FREE MEDIUM FOR CULTIVATION OF POSTNATAL CENTRAL NEURONS

[75] Inventors: Hiroshi Saito; Hiroshi Katsuki; Fumio Kawahara, all of Tokyo, Japan

[73] Assignee: Kyorin Pharmaceutical Co., Ltd., Tokyo, Japan

[21] Appl. No.: 387,321

[22] Filed: Feb. 13, 1995

[30] Foreign Application Priority Data

Feb. 18, 1994 [JP] Japan ..................... 6-44955

[51] Int. Cl.$^6$ ..................... C12N 5/00; C12N 5/02
[52] U.S. Cl. ..................... 435/404; 435/405; 435/406; 435/407; 435/381; 435/386; 435/387; 435/388; 435/394
[58] Field of Search ..................... 435/240.3, 240.31, 435/404, 405, 406, 407, 381, 386, 387, 388, 394

[56] References Cited

U.S. PATENT DOCUMENTS 5,135,866  8/1992  Heifetz et al. ............ 435/240.31
5,405,772  4/1995  Ponting ................... 435/240.21

FOREIGN PATENT DOCUMENTS 0 531 733  3/1993  European Pat. Off. .

OTHER PUBLICATIONS

Neurochemistry—A Practical Approach, edited by Turner et al., pp. 27–63 (1987).
Bottenstein et al., PNAS, 76(1): 514–17 (1979).
Bjare et al., Pharmac. Ther., 53:355–74 (1992).
Nutritional Requirements of Cultured Cells, edited by Katsuta, pp. 1–21 (1978).
Bottenstein et al., Experimental Research 125: 183–90 (1980).
Bottenstein et al., Cold Spring Harbor Conferences on cell Proliferation, vols. 6A and 6B, pp. 531–544 (1979).
Bottenstein, Cancer Treatment Reports. 65(Supple 2): 67–70 (1981).
Bottenstein, Advances in the Boisciences, 61:3–10 (1986).
Advances in Neuroblastoma Research, edited by Evans, pp. 161–170 (1980).
Methods for Serum–Free Culture of Neuronal and Lymphoid Cells, edited by Barnes et al., p/3–13 (1984).
Kawahara et al., Japenese Journal of Pharmacology, 64 (Suppl. 1): 236 P (Mar. 1994).
Developing and Regenerating Vertebrate Nervous Systems, edited by Coates et al., pp. 185–189 (1983).
Michler–Stuke et al., J. of Neuroscience Research, 7:215–28 (1982).
Pollack et al., J. Neurosurg., 73(1): 106–12 (1990).
Tixier–Vidal et al., Neuroscience, 17(1): 115–32 (1986).
Hutchins et al., Mol. Cell. Neurosci., 4(3): 25–58 (1993).
Francis et al., Soc. Neurosci Abstr., 17(1–2): 754 (1991).
Smits et al., Eur. J. Neurosci., 5(8):986–94 (1993).
Fischer, Neurosci. Lett., 28(3): 325–30 (1982).
Hunter et al. Dev. Brain Res., 54: 235–48 (1990).
Advances in Cellular Neurobiology, vol. 4, edited by Fedoroff, pp. 333–379 (1983).
Kushima et al., Brain Res., 598: 264–70 (1992).
Yamashita et al., Brain Res., 594: 215–20 (1992).
Brain Research, vol. 651, 1994, pp. 101–107, F. Kawahara, et al., "Primary Culture of Postnatal Rat Suprachiasmatic Neurons in Serum–Free Supplemented Medium".
Chapter 2 of R.P. Saneto and J.de Vellis Neuronal and glial cells: cell culture of the central nervous system, pp. 27–63.
Sigma Catalog pp. 64–67 (1995).
Rabovsky J et al., J. Environ. Path. Toxicol. Oncol. 6(3–4): 339–44 (1986).
Kane MT, J. Reprod and Fertility 69(2):555–8 (1983).
Lystade, In Vitro Cellular Develop. Biol. Animal, 30A (9) 568–73 (1994).
McKiernan SH, In Vitro Cellular Developmental Biol. 28A (3PT1):154–6 (1992).
Congote LF, In Vitro Cellular Developmental Biol. 23 (5): 361–6 (1987).

*Primary Examiner*—Sandy Saucier
*Attorney, Agent, or Firm*—Oblon, Spivak, McClelland, Maier & Neustadt, P.C.

[57] ABSTRACT

Disclosed is a synthetic medium with PDGF, vitronectin, IL-1β and BSA added to Eagle's minimum essential medium or medium with transferrin, insulin, progesterone and putrescine further added thereto. When cultivating the postnatal central neurons using the inventive medium, there are effects such that good attachment to substrate, extension of neuritic processes and maintenance of survival are achieved, that more stable sure cultivation becomes possible as well over the astrocyte-conditioned medium used hitherto, and the like.

7 Claims, 1 Drawing Sheet

SERUM-FREE MEDIUM FOR CULTIVATION OF POSTNATAL CENTRAL NEURONS

BACKGROUND OF INVENTION

The present invention relates to a serum-free medium useful for the cultivation of postnatal central neurons.

The central nervous system disorders represented by senile dementia, vascular lesion or encephalopathia due to cerebral lesion have become serious problems with the magnification of advanced age society. Hence, the development of therapeutic drugs for these diseases is desired earnestly. The cultivation system of neurons has very significant implications for the studies on the mechanism of regeneration and heeling processes of cell and the exploration of drugs acting on these processes.

The cultivation of neurons is performed usually using media with animal sera as bovine serum added to synthetic medium. The cultivation of postnatal central neurons is more difficult, which has succeeded only on the monolayer of astroglial cells (Brain Research, 598, 264–270 (1992)) or in the astrocyte-conditioned medium (ACM)(Brain Research, 594, 215–220 (1992)). Here, the term "postnatal" in this specification implies a state of neurons differentiated and matured functionally.

However, a signification problem arising when actually performing the cultivation of postnatal central neurons is the differences of quality between lots of serum, and the quality fluctuation of the cultivation of astroglial cells. Depending on the lots of serum or ACM, difference appears in the results of cultivation, and, unless good serum, monolayer or ACM can be secured, even the continuation of experiment becomes doubtful. While various hormones, growth factors, etc. are investigated as additives replaceable to such fluctuating factors, no materials with sufficient effect have ever been developed.

A serum-free stable medium that allows to cultivate always under same conditions can offer very high usefulness for the cultivation of neurons, and, still more, it satisfies a strong requirement for making it possible to cultivate postnatal central neurons. Namely, the invention has an objective to provide a novel medium for neurons, in particular for postnatal central neurons, which enables always stable attachment of neurons to the substrate, extension of neuritic processes and maintenance of survival, and thereby to provide a suitable culture condition which needs no serum with inconsistent effect, no astrocyte monolayer with difficult control or no ACM containing unknown factors as conventional.

SUMMARY OF THE INVENTION

The constitution of the invention for achieving such objective comprises following technical means.

(1) A serum-free medium for postnatal central neurons characterized by containing platelet-derived growth factor (PDGF) and bovine serum albumin (BSA) as effective ingredients.

(2) The serum-free medium for postnatal central neurons additionally containing either or both vitronectin and interleukin-1 beta (IL-1β) as effective ingredient(s) in the serum-free medium as described above in (1).

(3) A serum-free medium for postnatal central neurons characterized by containing PDGF, BSA, vitronectin and IL-1β as effective ingredients.

DETAILED DESCRIPTION OF THE INVENTION

Figure 1:
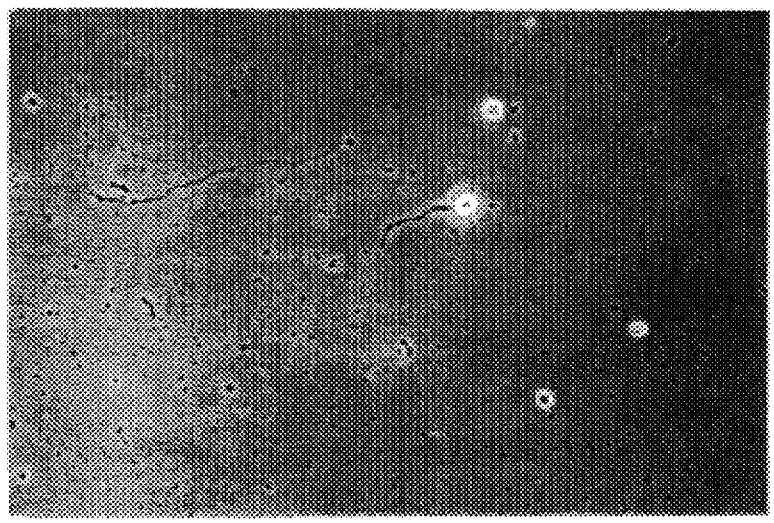
FIG. 1 is an image photograph by phase contrast microscope showing a morphology of suprachiasmatic nucleus neurons of 3-week-old postnatal rat with neuritic processes extended in the inventive medium (bar at right bottom in figure indicates 100 μm).

The Eagle's minimum essential medium (EEM), modified Eagle's medium (MEM), etc. known as basal media in this area could not be used for the cultivation of postnatal central neurons, unless adding the serum thereto. As in the invention, however, if allowing PDGF and BSA to be contained in the basal medium, the cultivation of postnatal central neurons has been achieved without adding the serum. Moreover, it has become clear that, if performing the cultivation of postnatal central neurons by allowing vitronectin and IL-1β to be contained in the basal medium in addition to PDGF and BSA, then more preferable cultivation results can be obtained.

As the basal media to be used in the invention, known media such as EEM and MEM used commonly in various cultivations of cells, not restricting to neurons, can be mentioned.

The concentrations of each ingredient to be contained in the medium are preferable to be 0.1 to 10 ng/mL for PDGF, 0.1 to 0.5% for BSA, 0.01 to 1.0 μg/mL for vitronectin and 0.1 to 10 U/mL for IL-1β. Further, more preferable concentrations of each ingredient are 0.5 to 1.0 ng/mL for PDGF, 0.1 to 0.2% for BSA, 0.05 to 0.5 μg/mL for vitronectin and 0.5 to 1.0 U/mL for IL-1β.

Moreover, upon cultivation, one or not less than two kinds of transferrin, insulin, progesterone, putrescine, etc. may be added to the inventive medium as additive(s).

When cultivating the postnatal central neurons using the medium obtained according to the invention, the proliferation of glial cells being found in the system with serum added is low, thus it is not required to add an inhibitor against the proliferation of glial cells. In particular, even under conditions difficult in the maintenance of survival as those of the low-density cultivation, the effect of the inventive medium is remarkable, and good attachment of neurons to the substrate, extension of neuritic processes and maintenance of survival can be perceived. For performing the cultivation of neurons, the inventive medium is very useful, offering a very large convenience industrially.

In following, the invention will be illustrated more concretely based on the examples, but the invention is not confined to these.

Referential Example 1

A medium with L-glutamine (0.29 g/L, Wako pure Chemical Industries, Ltd.), sodium pyruvate (0.11 g/L, Wako pure Chemical Industries, Ltd.), glucose (9.0 g/L, Wako pure Chemical Industries, Ltd.), sodium hydrogencarbonate (2 g/L, Wako pure Chemical Industries, Ltd.) and sodium selenite (30 nM, Wako pure Chemical Industries, Ltd.) added to Eagle's minimum essential medium (Nissui pharmaceutical Co.,Ltd.) was prepared (hereinafter referred to as MEM).

Referential Example 2

A medium with transferrin (100 μg/mL, Sigma), insulin (5 μg/mL, Becton-Dickinson), progesterone (20 nM, Sigma) and putrescine (100 μM, Sigma) added to MEM prepared similarly to Referential example 1 was prepared (hereinafter referred as MEM+TIPS).

Example 1

BSA (0.1%, Sigma), PDGF (0.5 ng/mL, Chemicon International Inc.), IL-1β (0.5 U/mL, Boehringer), and vitronectin (0.5 µg/mL, Sigma) were added to MEM prepared similarly to Referential example 1 to prepare a medium for postnatal central neurons.

Example 2

BSA (0.1%, Sigma), PDGF (0.5 ng/mL, Chemicon International Inc.), IL-1β (0.5 U/mL, Boehringer) and vitronectin (0.5 µg/mL, Sigma) were added to MEM +TIPS prepared similarly to Referential example 2 to prepare a medium for postnatal central neurons.

Testing Example

Using respective media prepared in referential examples and examples, the cultivations of central neurons were performed. According to Brain Research, 594, 215–220 (1992), slices of hypothalamus were made from the brain of 3-week-old postnatal rat, which were enzymatically digested in turn with pronase (0.02%, Calbiochem) and thermolysin (0.02%, Sigma), each for 30 minutes at 37° C. After enzyme solution was removed, the suprachiasmatic nuclei of hypothalamus were punched out, which were pipetted with glass capillary to obtain a cell dispersion. Onto a plastic plate (Nunc® of Inter Med or Falcon® of Becton-Dickinson) coated with 0.1% polyethyleneimine beforehand, this cell suspension was added at 50 to 150 µL/well, which was cultivated for 3 weeks at 37° C. in a carbon dioxide gas (5%)-air incubator. The cells were observed over time under microscope.

When performing the cultivation with media prepared in referential examples, no surviving cells were recognized.

When using the inventive media, the proliferation of glial cells was low and, over a long period of time from 3 to 5 days after start of cultivation to around 14 days, good attachment of neurons, extension of neuritic processes and maintenance of survival were recognized. Moreover, the fact that these cells were neurons was identified by the immuno staining method using antibody against MAP 2, a protein specific for neurons.

In FIG. 1, a phase contrast photomicrograph of suprachiasmatic nucleus neurons dissociated from 3-week-old postnatal rat brain, the neuritic processes of which was extended in the inventive medium, is shown.

What is claimed is:

1. A serum-free medium for culturing postnatal central neurons comprising 0.1–0.2% bovine serum albumin, 0.5–1.0 ng/mL platelet-derived growth factor, 0.1–10 U/mL IL-1β and 0.05–0.5 µg/mL vitronectin.

2. The serum-free medium for postnatal central neurons of claim 1, further comprising a basal media.

3. The serum-free medium for postnatal central neurons of claim 2, wherein said basal media is selected from the group consisting of Eagle's minimum essential medium and modified Eagle's medium.

4. The serum-free medium of claim 1, comprising 0.5 to 1.0 U/mL of IL-1β.

5. A method for culturing postnatal central neurons comprising:

culturing postnatal central neuron cells in a serum-free medium comprising 0.1–0.2% bovine serum albumin, 0.5–1.0 ng/mL platelet-derived growth factor, 0.1–10 U/mL IL-1β and 0.05–0.5 µg/mL vitronectin.

6. The method of claim 5, wherein said serum-free medium does not comprise an added inhibitor against the proliferation of glial cells.

7. The method of claim 5, wherein said serum-free medium comprises 0.5 to 1.0 U/mL of IL-1β.

* * * * *